(12) United States Patent
Csuk et al.

(10) Patent No.: US 8,629,300 B2
(45) Date of Patent: Jan. 14, 2014

(54) ARYLAMINE-SUBSTITUTED DIVINYL FLUORENES AND THEIR USE FOR ELECTROPHOTOGRAPHIC APPLICATIONS, AND FOR OLEDS (ORGANIC LIGHT EMITTING DEVICES)

(75) Inventors: Rene Csuk, Halle (DE); Gunter Mattersteig, Ulm (DE); Marc Herm, Merseburg (DE)

(73) Assignee: Sensient Imaging Technologies GmbH, Bitterfeld-Wolfen (DE)

( * ) Notice: Subject to any disclaimer, the term of this patent is extended or adjusted under 35 U.S.C. 154(b) by 645 days.

(21) Appl. No.: 12/518,935

(22) PCT Filed: Dec. 11, 2007

(86) PCT No.: PCT/EP2007/010762
§ 371 (c)(1),
(2), (4) Date: Dec. 29, 2009

(87) PCT Pub. No.: WO2008/071376
PCT Pub. Date: Jun. 19, 2008

(65) Prior Publication Data
US 2010/0094056 A1  Apr. 15, 2010

(30) Foreign Application Priority Data
Dec. 13, 2006 (DE) .......................... 10 2006 059 215

(51) Int. Cl.
*C07C 211/54* (2006.01)
*H01L 51/50* (2006.01)
(52) U.S. Cl.
USPC .......................................... 564/305; 428/917
(58) Field of Classification Search
USPC .......................................... 564/305; 428/917
See application file for complete search history.

(56) References Cited

U.S. PATENT DOCUMENTS

| | | | |
|---|---|---|---|
| 6,515,182 B2 | 2/2003 | Hosokawa et al. | |
| 6,517,957 B1 | 2/2003 | Senoo et al. | |
| 6,555,959 B1 * | 4/2003 | Nii ................ | 313/506 |
| 6,657,224 B2 | 12/2003 | Shi et al. | |
| 2001/0033944 A1 | 10/2001 | Onikubo et al. | |
| 2003/0030059 A1 | 2/2003 | Shi et al. | |
| 2003/0091859 A1 | 5/2003 | Cho et al. | |
| 2005/0067951 A1 | 3/2005 | Richter et al. | |
| 2006/0022193 A1 | 2/2006 | Williamson et al. | |

FOREIGN PATENT DOCUMENTS

| | | |
|---|---|---|
| DE | 19829055 | 1/1999 |
| DE | 102004020046 | 7/2005 |
| DE | 102004029695 | 1/2006 |
| DE | 102005003634 | 7/2006 |
| DE | 102005036696 | 2/2007 |
| EP | 795791 | 9/1997 |
| EP | 0848579 | 6/1998 |
| EP | 1029909 | 8/2000 |
| JP | 08-292586 | 11/1996 |
| JP | 10-265773 | 10/1998 |
| JP | 10-302960 | 11/1998 |
| JP | 2001-273977 | 10/2001 |
| JP | 2008-074708 | 4/2008 |
| KR | 2005-0081981 | 8/2005 |
| WO | 99/53242 | 10/1999 |
| WO | 01/56091 | 8/2001 |
| WO | 03/064373 | 8/2003 |

OTHER PUBLICATIONS

Suo et al. (Org. Lett., vol. 7, No. 22 (2005), p. 4807-4810).*
Pan et al. (Mat. Res. Soc. Symp. Proc., v. 734 (2003), p. B9.24.1-6).*
Han et al. (Journal of Molecular Structure: THEOCHEM (2007), 802(1-3), 67-74) (available online Sep. 19, 2006).*
Belfield, K.D. et al., "New highly efficient two-photon fluorescent dyes," Proceedings of SPIE—The International Society for Optical Engineering, 5351 (Organic Photonic Materials and Devices VI), (2004) 173-180.
Kauffman, J.M. et al., "Diarylamino groups as photostable auxofluors in 2-benzoxazolylfluorene, 2,5-diphenyloxazoles, 1,3,5-hexatrienes, 1,4-distyrylbenzenes, and 2,7-distyrylfluorenes," J. Org. Chem. (2003) 68 (3):839-853.
Kay, K-Y. et al., "Electroluminescent properties of novel fluorene derivatives with aromatic amine moieties," Mol. Crystals and Liquid Crystals (2006) 444:121-128, and Chemical Abstracts Database Access. No. 2006:88283.
Kim, O-K. et al., "New class of light-emitting polymers/oligomers," Proceedings of SPIE—The International Society for Optical Engineering, 3955 (Liquid Crystal materials, Devices and Flat Panel Displays), (2000) 134-140.

(Continued)

*Primary Examiner* — Robert Havlin
(74) *Attorney, Agent, or Firm* — Michael Best & Friedrich LLP

(57) ABSTRACT

The invention relates to arylamine-substituted divinyl fluorenes. The invention is based on the object of providing photoconductors having good durability, high sensitivity, and low residual potential. The task is to detect new perforated conductors, which can be used in electrophotography, for copying, and in the OLED field. The task is solved by the production of the title compounds, particularly of the formula (11).

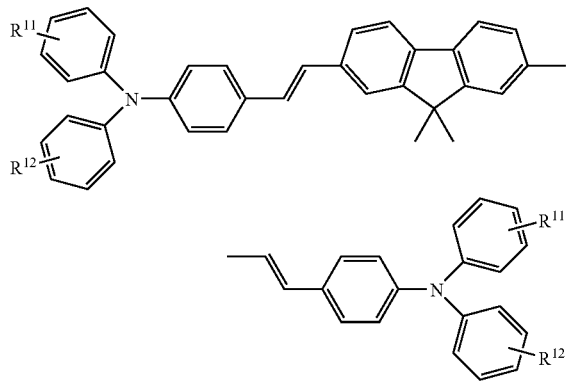

(11)

2 Claims, 1 Drawing Sheet

(56) References Cited

OTHER PUBLICATIONS

Kim, O-K. et al., "Oligothiophene as photonic/electronic property modulator," Optical Materials (2003) 21(1-3):559-564.

Lee, K-S. et al., "Optical power limiting properties of two-photon absorbing fluorene and dithienothiophene-based chromophores," Proceedings of SPIE—The International Society for Optical Engineering, 4991 (Organic Photonic Materials and Devices V), (2003) 175-182.

Liao, L. et al., "Efficient blue-green-emitting poly[(5-diphenylamino-1, 3-phenylenevinylene)-alt-(2,5-dihexyloxy-1, 4-phenylenevinylene)] derivatives," J. Polym. Sci. Part A: Polymer Chem. (2006) 44(7):2307-2315.

Mikroyannidis, J.A. et al., "Synthesis and photophysical characteristics of 2,7-fluorenevinylene-based trimers and their electroluminescence," J. Phys. Chem. B (2006) 110(41):20317-20326.

Palilis, L.C. et al., "Bright and efficient blue light-emitting diodes based on conjugated polymer blends," SPIE, Part of the SPIE Conference on Organic Light-Emitting Materials and Devices III, Denver, Colorado (1999) 3797:383-397.

Pan, M. et al., "A new approach to design light emitting devices using electroactive dyes," Materials Research Society Symposium Proceedings, 734 (2003) B9.24.1, 6 pages.

Park, S.H. et al., "Fabrication of a bunch of sub-30-nm nanofibers inside microchannels using photopolymerization via a long exposure technique," Appl. Phys. Letts. (2006) 89(17):173133/1-173133/3.

Patra, A. et al., "Electroluminescence properties of systematically derivatized organic chromophores containing electron donor and acceptor groups," Chem. Matls. (2002) 14(10):4044-4048.

Su, H-J. et al., "Color tuning of a light-emitting polymer: polyfluorene-containing pendant amino-substituted distyrylarylene units," Adv. Funct. Matl. (2005) 15(7):1209-1216.

Su, Y.Z. et al., "Amorphous 2,3-substituted thiophenes: potential electroluminescent materials," Chem. Materials (2002) 14(4):1884-1890.

Suo, Z. et al., "New fluorophores based on trifluorenylamine with very large intrinsic three-photon absorption cross sections," Org. Letts. (2005) 7(22):4807-4810.

United States Patent Office Action for U.S. Appl. No. 10/899,522 dated Jan. 8, 2009 (16 pages).

United States Patent Office Action for U.S. Appl. No. 10/899,522 dated Mar. 27, 2008 (19 pages).

International Search Report and Written Opinion for Application No. PCT/EP2007/010762 dated Apr. 2, 2008 (11 pages).

Chinese Patent Office Action for Application No. 200780049771.8 dated May 3, 2012 (6 pages—English Translation and Original).

Han et al., "Calculation on the one- and two-photon absorptions properties for two series of dimethylfluorene core derivatives" Journal of Molecular Structure:THEOCHEM, 2007, 802, 67-74.

Corredor et al., "One- and two-photon photochemical stability of linear and branched flourene derivatives" Journal of Photochemistry and Photobiology A:Chemistry, 2006, 184, 105-112.

Park et al., "Direct Nano-patterning methods using nonlinear absorption in photopolymerization induced by a femtosecond laser" Journal of Nonlinear Optical Physics & Materials, 2005, vol. 14, No. 3, 331-340.

Japanese Patent Office Action for Application No. 2009-7014568 dated Feb. 4, 2013 (11 pages—Including English Translation).

Chinese Patent Office Action for Application No. 200780049771.8 dated May 2, 2013 (15 pages—English Translation and Original).

* cited by examiner

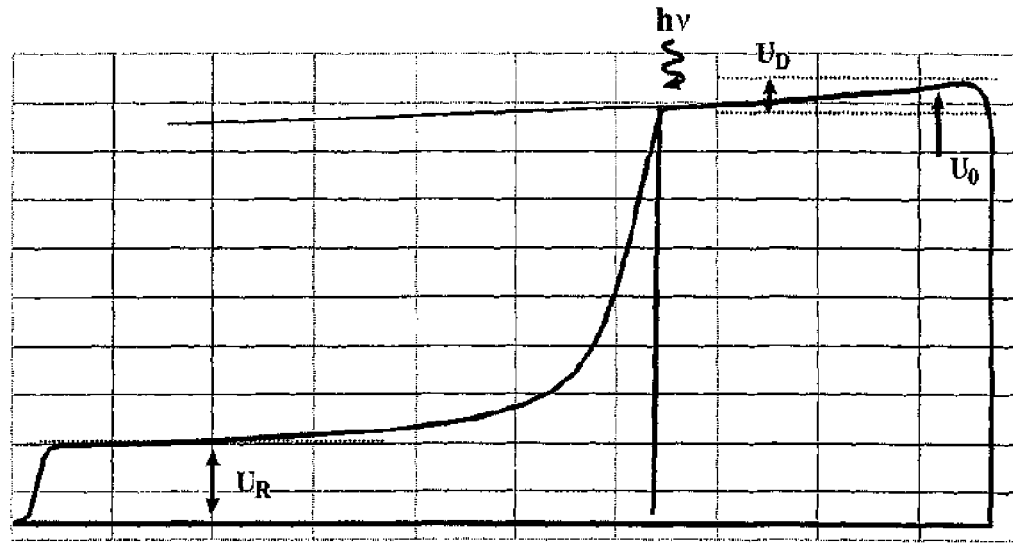

$U_D = 55V/3s$
$U_o = -880\ V$
$U_R = 160V$
$E_{0,5} = 0.182\ \mu Jcm^{-2}$

Fig. 1: Elektrophotographic discharge curve

$U_0$: Voltage present after charging the dual layer system in darkness
$U_D$: potential drop of the charged dual layer system in darkness
$U_R$: Voltage present after exposure of the dual layer system
$E_{0,5}$: electrophotographic sensitivity in the inflection point of the discharge curve under exposure in the dual layer system (550 nm)

| LL | Polymer | $U_o$ [V] | $U_D$ [V/3s] | $U_R$ [V] | $E_{0,5}$ [μJ/cm²] |
|---|---|---|---|---|---|
| MH15 | | -780 | 47 | 5 | 0,117 |
| MH15 | | -740 | 40 | 22 | 0,12 |
| MH15 | | -800 | 58 | 10 | 0,12 |
| MH15 | | -820 | 47 | 10 | 0,126 |
| MH15 | | -770 | 58 | <10 | 0,123 |
| MH15 | | -820 | 50 | <10 | 0,125 |

Fig.2

ARYLAMINE-SUBSTITUTED DIVINYL FLUORENES AND THEIR USE FOR ELECTROPHOTOGRAPHIC APPLICATIONS, AND FOR OLEDS (ORGANIC LIGHT EMITTING DEVICES)

CROSS-REFERENCE TO RELATED APPLICATIONS

This patent application is a national stage filing under 35 U.S.C. 371 of International Application No. PCT/EP2007/010762, filed on Dec. 11, 2007, which claims foreign priority benefits to German Patent Application No. 10 2006 059 215.8, filed on Dec. 13, 2006. These applications are incorporated herein by reference in their entireties.

The invention relates to new arylamine-substituted divinyl fluorenes and their use for electrophotographic applications and for organic light emitting diodes and for new materials and agents.

The use of tri-arylamines in electrophotography has been known for a long time. Furthermore, it was discovered that tri-arylamine-substituted hole conductors (defect electron conductors) with an extended π-conjugation system which is obtained by the incorporation of vinyl-butadienyl- and styryl-groups often have a substantially increased hole mobility compared to those without extension (EP795791 Mitsubishi Chemical). The increase with regard to hole mobility in charge transport materials is of basic importance for increasing the efficiency of electrophotography in laser printers and copy machines and the efficiency of electroluminescence in OLEDs.

It has been discovered that a low hole mobility in the charge transport layer reduces the sensitivity of the imaging unit of laser printers and laser copy machines and increases the residual potential (DE19829055). Due to the reduction of the sensitivity and the increase of the residual potential a reduced printing density is produced. It is also known that the hole mobility in the charge transport layer is reduced if the concentration of the charge transport means is reduced in the binder material which is conventionally a polycarbonate. To avoid this effect the concentration of the charge transport material is increased which, however, results in a reduced durability of the charge transport layer. It has been discovered that the above indicated difficulties can be overcome if a binder resin having a high molecular weight is used. High molecular resins, however, have a limited solubility in the majority of solvents producing defects like cloud forming in the photo conducting film if the film is prepared according to the dip method. This substantially reduces the productivity of the of the photo-conductor.

It is therefore obvious to use hole conductor material having a substantially higher defect electron mobility than that of the conventional hole conductors like, for example, TPD (N,N'-Diphenyl-N,N'-di-m-tolyl-benzidine) or N,N'-diphenyl-N,N'-di-naphth-1-yl-benzidine (α-NPD).

In this way, the concentration of charge transport material can be reduced and thus the stability of the hole carrier layer can be increased. It also useful that the printing speed can be increased by using hole conductors having a high mobility.

Well balanced hole and electron currency densities in the respective charge transport materials are required for an efficient electroluminescence in heterostructure OLEDs. The recombination probability and thus the quantum yield of electroluminescence can be substantially increased if the defect electron mobility in the hole transport layer is associated with the electron mobility in the electron transport layer. The incorporation of additional vinyl, butadienyl, and styryl groups into the basic structure of the hole conductor should effect a precise adjustment of the hole mobility and thus an optimal adjustment to the electron mobilities.

9,9-dialkyl-N,N,N',N'-tetraryl-9H-fluoren-2,7-diamines in which the triaryl-amine-groups are part of the fluorine basic framework and that have extensive sterically demanding substituents for achieving a high glass transition temperature are claimed in US 2005/0067951A1 (Richter, Lischewski, Sensient). These are suitable as hole conductor materials for electrophotography and for OLED applications. New divenyl-fluorene compounds which are used as optical brighteners, sensitizers for light-sensitive materials or educts for polymeric electroluminescence materials are claimed in US2006/0022193A1. The cited patent specification also discloses the synthesis of divinyl-fluorene compounds. Starting with fluorene a dialkylation of the C-9-atom is performed using alkyl bromide and sodium hydride. In the following step, a reaction with paraformaldehyde and hydrogen bromide in acidic acid is performed producing the corresponding 2,7-bis(bromomethyl)-9,9-dialkyl fluorene. The subsequent reaction with triethyl phosphite produces 2,7-bis(diethylphosphonate methyl)-9,9-dialkyl fluorene. In a subsequent Wittig-Horner olefination this compound is reacted with an aldehyde or ketone in the presence of a base producing the corresponding 9,9-dialkyl-2,7-divinyl-9/-/-fluorenes.

DE 102005036696 already proposed carbaldehyde and acryl-aldehyde-substituted arylamines and their acetales as precursors especially for electrophotographic applications and for OLEDs as well as for new materials and agents.

The aim of the invention is wear resistant photo conductor having excellent durability, high sensitivity and low residual potential.

The aim of the invention is to produce compounds and to propose their application in hole conductors having substantially improved hole conductor mobilities. These compounds should be new materials or—if already known—have not been considered for the proposed application.

The invention is based on the scientific idea to produce new potential hole conductors having a high hole conductor mobility and which are suitable for electrophotographic applications by inserting a group of well polarisable π-electrons—like vinyl-groups—into arylamino structures that are in direct conjugation with a fluorene molecule.

In this regard, suitable candidates are triarylamine derivates of the divinylfluorene.

The present invention claims compounds of formula 1 and their application in electrophotography and in OLEDs and for new agents and materials.

The following definitions apply:

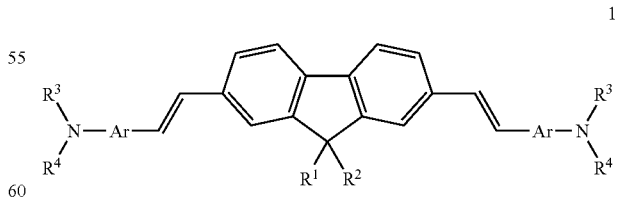

Group Ar in the general chemical formula 1 is an homoaromatic or heteroaromatic group which is where appropriate benzoannelated, for example, phenylene, naphthylene, thienylene, furylene, or antracenylene units, where appropriate substituted by alkyl, aryle or arylalkyle groups, biphenylene units according to formula 6, fluorenylne, dibenzofuranylene, dibenzothiophenylene, carbazolylene or dibenzosilolylene units according to formula 7 wherein unit A is selected from the following structures.

$R^1$ and $R^2$ are independently an branched or linear alkyl group ($C_1$ to $C_{20}$ alkyl group), a branched or linear unsaturated carbohydrate group, a cycloalkyle group (e.g. cyclohexyl group) or an aryl group (e.g. phenyl, alkylphenyle, naphthyl, alkylnaphthyl, biphenylyl, alkylbiphenylyl, stilbenyl or tolanyl group), a branched or linear alkoxy group.

$R^3$ and $R^4$ are independently phenyl, alkylphenyl, in particular Me-thylphenyle, biphenylyl, alkylbiphenyle, naphthyl, alkylnaphthyl, phenanthrenyl, alkylphenanthrenyl, anthracenyl, alkylanthracenyl, fluorenyl, alkylfluorenyl, triaryl-methyl-aryl or triarylsilyl-aryl.

The compounds can be produced according to the following formula scheme 1:

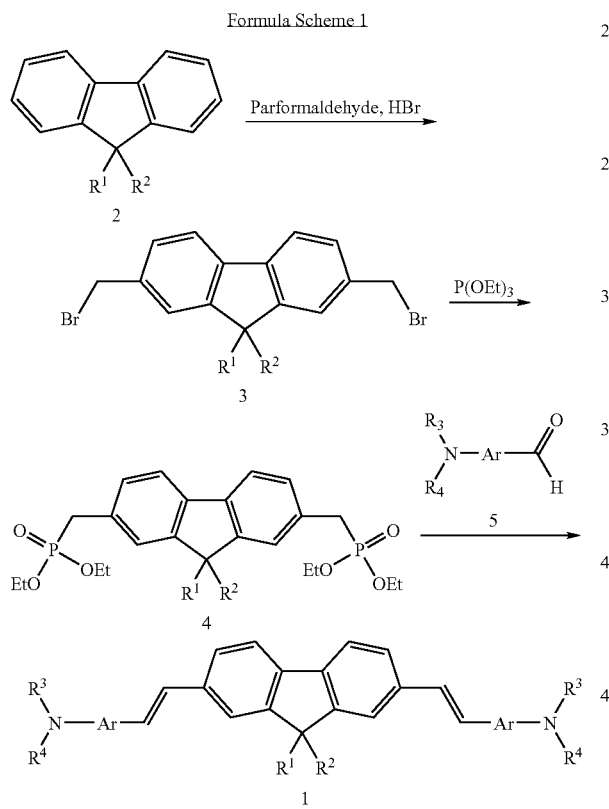

9,9-dialkyle fluorene 2 is 2,7-bishalomethylated using paraformaldehyde and HBr. Intermediate product 3 is reacted with triethylphosphite to the corresponding 2,7-bis(dialkylphosphonatomethyle)-9,9-dialkylfluorene 4 in the second step, which produces in the third step by reaction with an aromatic aldedhyde the desired 2,7-divenyl fluorene 1. This reaction is performed analogous to the method in US2006/0022193A1. Thus, no protection of the method for producing divenyl fluorene can be claimed.

However, product protection for the trialyldervates of the 2,7-divinyl-9H-fluorene 1 which can be obtained in this way is claimed. No differently substituted diaryl-aminobenzaldehydes 5 are claimed in the cited application, in particular, no differentially substituted diarylamino benzaldehydes, with reference to the Wittig-Horner reactions described in said application.

The following definitions apply for the aldehydes of the triarylamine 5:

Group Ar in the general chemical formula 5 is an homoaromatic or heteroaromatic group which is where appropriate benzoannelated, for example, phenylene, naphthylene, thienylene, furylene, or antracenylene units, where appropriate substituted by alkyl, aryle or arylalkyle groups, biphenylene units according to formula 6, fluorenylne, dibenzofuranylene, dibenzothiophenylene, carbazolylene or dibenzosilolylene units according to formula 7 wherein unit A is selected from the following structures.

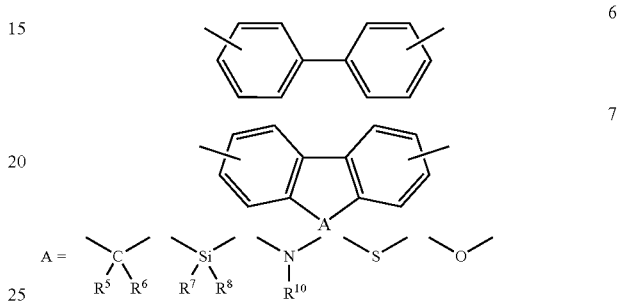

$R^3$ and $R^4$ are independently phenyl, alkylphenyl, in particular Me-thylphenyle, biphenylyl, alkylbiphenyle, naphthyl, alkylnaphthyl, phenanthrenyl, alkylphenanthrenyl, anthracenyl, alkylanthracenyl, fluorenyl, alkylfluorenyl, triaryl-methyl-aryl or triarylsilyl-aryl.

In the first embodiment compounds of the formula 8 are claimed:

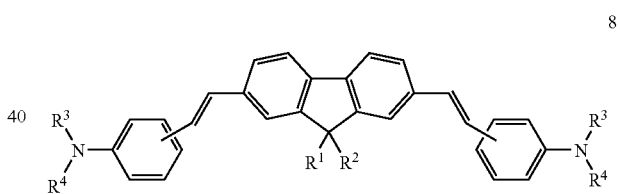

$R^1$ and $R^2$ are independently a branched or linear alkyl group ($C_1$ to $C_{20}$ alkyl group), a branched or linear unsaturated carbohydrate group, a cycloalkyle group (e.g. cyclohexyl group) or an aryl group (e.g. phenyl, Alkylphenyle, naphthyl, alkylnaphthyl, biphenylyl, alkylbiphenylyl, stilbenyl or tolanyl group), a branched or linear alkoxy group.

$R^3$ and $R^4$ are independently phenyl, alkylphenyl, in particular Me-thylphenyle, biphenylyl, alkylbiphenyle, naphthyl, alkylnaphthyl, phenanthrenyl, alkylphenanthrenyl, anthracenyl, alkylanthracenyl, fluorenyl, alkylfluorenyl, triaryl-methyl-aryl or triarylsilyl-aryl.

In the first preferred embodiment compounds of the formula 9 are claimed:

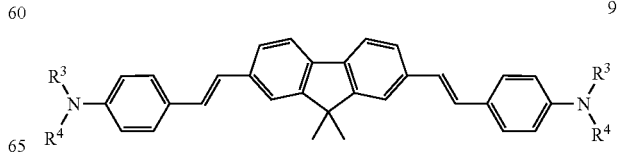

wherein:

R³ and R⁴ are independently phenyl, alkylphenyl, in particular Me-thylphenyle, biphenylyl, alkylbiphenyle, naphthyl, alkylnaphthyl, phenanthrenyl, alkylphenanthrenyl, anthracenyl, alkylanthracenyl, fluorenyl, alkylfluorenyl, tri-aryl-methyl-aryl or triarylsilyl-aryl.

Preferred are compounds of formula 10:

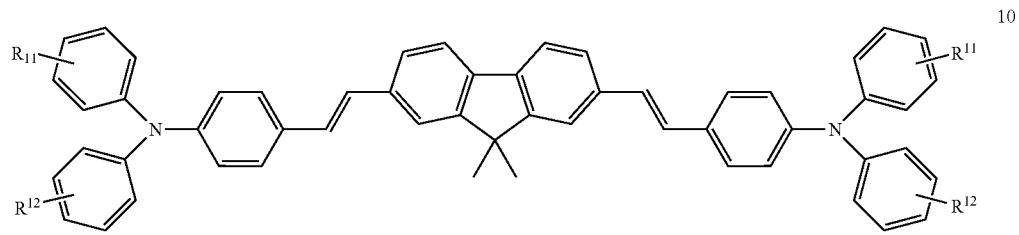

$R^{11}$ and $R^{12}$ are independently H, a branched or linear alkyl group ($C_1$ to $C_{20}$ alkyl group), a branched or linear unsaturated carbohydrate group, a cycloalkyle group (e.g. cyclohexyl group) or an aryl group (e.g. phenyl, Alkylphenyle, naphthyl, alkylnaphthyl, biphenylyl, alkylbiphenylyl, stilbenyl or tolanyl group), a branched or linear alkoxy group.

An even more preferred embodiment are compounds of the formula 11, wherein:

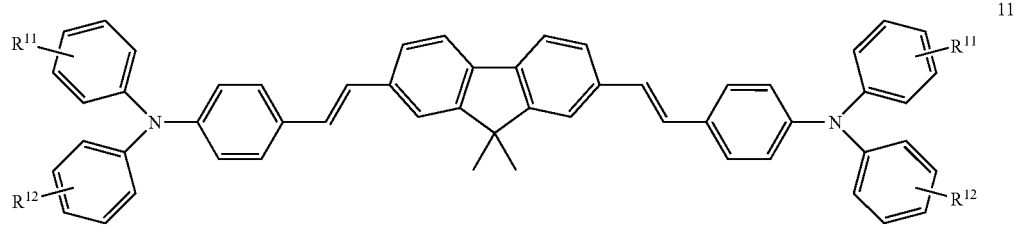

$R^{11}$ and $R^{12}$ are independently H or a methyl group which can be located in ortho-metha and para position to the amino group.

The most preferred embodiment is a compound of formula 12 wherein R11 and R12 each represent a methyl group in para position to the amino group.

The invention shall be illustrated by reference to the following examples.

EXAMPLE 1

2,7-Bis(bromomethyl)-9,9-dimethylfluorene 3

Finely pulvered 9,9-Dimethylfluoren (Sensient, 20.0 g, 102.9 mmol) and paraformaldehyde (15.0 g, 500 mmol) was provided in a 250 ml round bottom flask with several necks and ground glass joints ("Sulfierkolben") and ground thermometer. Then 100 ml of 33% HBr in glacial acidic acid and a magnetic stir bar were added. The flask was sealed with plugs and stirred at 45° C. for 30 h. The white solid that formed was aspirated and washed with a little amount of ice cold water (2×25 ml) and ice cold methanol (2×20 ml). Finally, recrystallization in glacial acidic acid was performed.

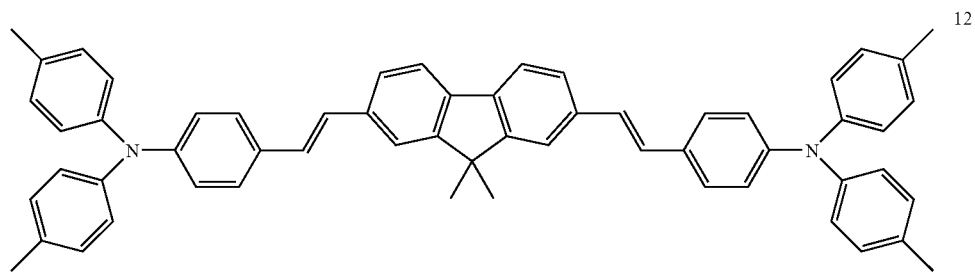

After the reaction had cooled down the reaction was incubated over night, aspirated, and washed again with ice cold methanol (2×20 ml).

Over night incubation at room temperature and 8 hours incubation in a cabinet desiccator at 70° yielded 25.02 g (65.8 mmol, 64%) of a white solid (DC: cyclohexane: Dichlormethane=5:1, $R_f$=0.45).

EXAMPLE 2

2,7-Bis(diethoxyphosphinylmethyl)-9,9-dimethylfluorene 4

2,7-bis(bromomethyl)-9,9-dimethylfluorene (25.00 g, 66 mmol) and 25 ml triethyl phosphite (150 mmol) were provided in a 100 ml flask with three necks with a cross stirbar, argon inlet, ground thermometer and a distillation bridge with a Vigreux column under argon flushing. The oil bath below was carefully heated to 120-125° C. At 65-70° C. gassing commenced and a clear stirable mixture formed. Ethyl bromide was distilled of using low argon flushing at 75-80° C. After distilling the majority of the ethyl bromide the heating continued at 160° C. for one hour. After cooling down to an oil bath temperature of 100° C. and under continuous stirring the argon flashing was stopped and a membrane pump was connected to remove excess trieethyl phosphite. To achieve this the oil bath temperature was increased to 150-160° C. When triethyl phosphite stopped being distilled the oil pump was removed and argon flushing resumed. After cooling down to 70° C. the liquid was decanted into a crystallizing dish. A viscous syrup-like clear liquid formed (31.2 g, 63.1 mmol, 95.6%). This crude product was used for the subsequent reaction since crystallisation did not start after several hours of incubation and grinding with a glass rod and or inoculation attempts.

EXAMPLE 3

2,7-Bis-(4-di-p-tolylaminophenylethenyl)-9,9-dimethyl-9H-fluorene (MH15) 1

2,7-Bis(diethoxyphosphinylmethyl)-9,9-dimethylfluorene (31.2 g, 63.1 mmol) and Dimethylformamid (431 ml) are subsequently provided in 1 l flask with two necks that was equipped with a magnetic stir bar, a gas inlet tube, and a drying tube and were stirred under argon flushing for 10 minutes. Aldehyde (Sensient, 38.1 g, 126.3 mmol) was added while continuously stirring and argon flushing. After complete dissolution the flask was cooled with ice from the outside and then tert-BuOK (16.94 g, 151.0 mmol) was added in portions.

While continuously flushing with argon and cooling with ice, stirring was continued for 45 minutes and then at room temperature for a further 20 hours. The reaction mixture initially turned dark red brown, later on green and by-and-by formed a suspension. Then the desired product was precipitated with a triple volume of methanol (1100 ml) while stirring and ice cooling continued for one hour. Aspiration was performed using a big frit, washing was performed three times with 150 ml of methanol and drying was performed in a cabinet desiccator at 50° C. over night. 44.2 g (56 mmol) (89%) of a yellow solid (crude product) was obtained which was then subjected to column chromatography. For this purpose a chromatography column 100 cm×12 cm of the company Neubert and silica gel 60 (0.063-0.2 mm) of the company Merck was used. The eluent was a mixture of cyclohexane and toluol (2:1). Ca. 4 kg silica gel and 9 liter eluent mixture were mixed in several portions to fill the column. Then a layer of see sand (2 cm) was carefully added as an overlay. In the meantime the crude product was dissolved in 1.5 liter of toluol and mixed with 300 g of silica gel. It was completely dried using a rotating evaporator and the solid-silica gel-mixture was carefully positioned on top of the sand layer. Subsequently a further eluent mixture (cyclohexane: toluol=2:1) was added and finally a second sand layer (2 cm) was applied as an overlay. The column was carefully filled with further eluent. The running time of the column was 4 hours and 22 liters of cyclohexane and 11 liters of toluol were consumed. Fractions of 1 liter each were collected. The desired product had an $R_f$ value of 0.89. Only those fractions were collected that showed a clear yellow spot during thin layer chromatography. The forerunnings yielding a slightly brownish spot which directly overlayed the main spot were discarded. Removal of the solvent with a rotating evaporator produced 37.4 g of a yellow solid which was subsequently dried in a cabinet desiccator at 100° C. for 12 hours. Finally, 36.4 g (73%) of a yellow crystalline solid were obtained (melting point 242-245° C.)

EXAMPLE 4

Solubility Analysis and Purification

Compound 12 complies with the solubility requirements set by the industry of 1 g substance/6 ml methylen chloride or THF. This compound was scaled up to 35 g. The compound was brought to an HPLC purity of >99.5% by using conventional purification methods, like e.g. recrystallization or column chromatography.

EXAMPLE 5

Production of Hole Conductor Layers and Electrophotographic Testing

The electrophotographic properties of the produced hole conductors were determined in a double layer system by the cooperation partner. For this purpose, a aluminated polyester support was coated with a dispersion of Y-titanyl phtalocyanin in polycarbonate/methylen chloride. The charge producing layer produced in this way after the drying was coated with a solution of the corresponding hole conductor in polycarbonate/methylen chloride and measured after drying.

To determine the electrophotographic properties the sequence of layers to be tested was charged negatively in darkness using a corotron wire ($U_0$). After a defined time the device is exposed to a defined quantity of light. The potential drop until exposure is referred to as dark decay ($U_D$). The electrophotographic sensitivity is the result of the half time of the discharge cycle multiplied with the irradiated light intensity. A typical discharge curve is presented in FIG. 1. For commercial use an electrophotographic sensitivity of at least 0.5 µJ/cm² has to be achieved with the sequence of layers used.

FIG. 1 shows a typical discharge curve.

FIG. 2 is a table of electrophotographic properties.

The invention claimed is:
1. Compounds of formula 11
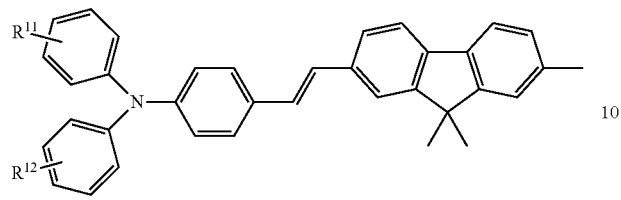
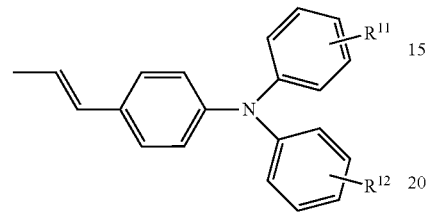
$R^{11}$ and $R^{12}$ are independently
a methyl group which can be located in ortho-metha and para position to the amino group.
2. A compound described by formula 12
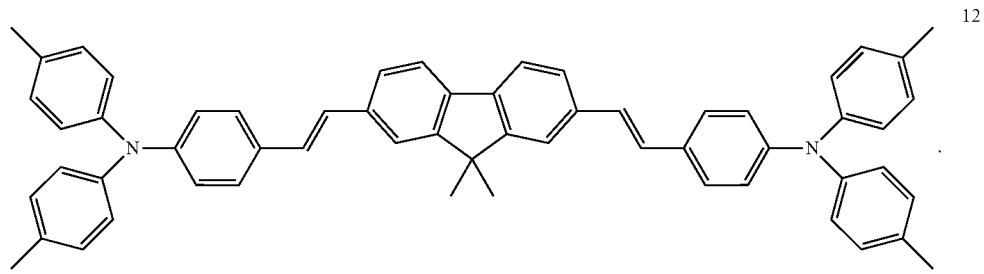
* * * * *

UNITED STATES PATENT AND TRADEMARK OFFICE
CERTIFICATE OF CORRECTION

PATENT NO.       : 8,629,300 B2                                              Page 1 of 1
APPLICATION NO. : 12/518935
DATED            : January 14, 2014
INVENTOR(S)      : Csuk et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 958 days.

Signed and Sealed this
Twenty-second Day of September, 2015

Michelle K. Lee
*Director of the United States Patent and Trademark Office*